United States Patent
Park et al.

(10) Patent No.: US 12,283,051 B2
(45) Date of Patent: Apr. 22, 2025

(54) METHOD FOR ANALYZING LESION BASED ON MEDICAL IMAGE

(71) Applicant: VUNO Inc., Seoul (KR)

(72) Inventors: Hyunho Park, Seoul (KR); Gwangbeen Park, Seoul (KR); Seungho Lee, Seoul (KR)

(73) Assignee: VUNO Inc., Seoul (KR)

( * ) Notice: Subject to any disclaimer, the term of this patent is extended or adjusted under 35 U.S.C. 154(b) by 572 days.

(21) Appl. No.: 17/556,529

(22) Filed: Dec. 20, 2021

(65) Prior Publication Data

US 2022/0198668 A1    Jun. 23, 2022

(30) Foreign Application Priority Data

Dec. 23, 2020 (KR) .................. 10-2020-0181634

(51) Int. Cl.
*G06T 7/00*    (2017.01)
*G06T 7/11*    (2017.01)
(Continued)

(52) U.S. Cl.
CPC .............. *G06T 7/0016* (2013.01); *G06T 7/11* (2017.01); *G06T 7/30* (2017.01); *G06T 7/62* (2017.01); *G06T 7/70* (2017.01); *G06V 10/25* (2022.01); *G06V 10/764* (2022.01); *G16H 30/40* (2018.01); *G16H 50/20* (2018.01); *G06T 2200/24* (2013.01); *G06T 2207/20081* (2013.01); *G06T 2207/20084* (2013.01); *G06T 2207/30064* (2013.01); *G06V 2201/032* (2022.01)

(58) Field of Classification Search
CPC . G06T 7/0016; G06T 7/62; G06T 7/11; G06T 7/30; G06T 7/70; G06T 2200/24; G06T 2207/20081; G06T 2207/20084; G06T 2207/30064; G16H 50/20; G16H 30/40; G06V 10/25; G06V 10/764; G06V 2201/032
USPC ........................................................ 382/128
See application file for complete search history.

(56) References Cited

U.S. PATENT DOCUMENTS 7,305,111 B2    12/2007    Arimura et al.
10,553,311 B2    2/2020    Lyman et al.
(Continued)

FOREIGN PATENT DOCUMENTS

JP    2009-502232 A    1/2009
JP    2019141478 A    8/2019
(Continued)

OTHER PUBLICATIONS

Jacobs et al., "Solid, Part-Solid, or Non-Solid?: Classification of Pulmonary Nodules in Low-Dose Chest Computed Tomography by a Computer-Aided Diagnosis System," *Investigative Radiology*, 50(3):168-173, Mar. 2015.

*Primary Examiner* — Michael R Neff
(74) *Attorney, Agent, or Firm* — Seed IP Law Group LLP

(57) ABSTRACT

Disclosed is a method for analyzing a lesion based on a medical image, which is performed by a computing device. The method may include: obtaining positional information of a suspicious nodule which exists in the medical image; generating a mask for the suspicious nodule based on a patch of the medical image corresponding to the positional information; and determining a class for a state of the suspicious nodule based on the patch of the medical image and the mask for the suspicious nodule.

18 Claims, 8 Drawing Sheets

(51) Int. Cl.
    *G06T 7/30*         (2017.01)
    *G06T 7/62*         (2017.01)
    *G06T 7/70*         (2017.01)
    *G06V 10/25*       (2022.01)
    *G06V 10/764*      (2022.01)
    *G16H 30/40*       (2018.01)
    *G16H 50/20*       (2018.01)

(56)         References Cited

U.S. PATENT DOCUMENTS

| | | |
|---|---|---|
| 2005/0063579 A1 | 3/2005 | Lee et al. |
| 2007/0019852 A1 | 1/2007 | Schildkraut et al. |
| 2009/0123049 A1 | 5/2009 | Dehmeshki |
| 2010/0111386 A1* | 5/2010 | El-Baz .................. G06T 7/143 |
| | | 382/128 |
| 2017/0039737 A1 | 2/2017 | Madabhushi et al. |
| 2021/0019880 A1* | 1/2021 | Chan .................. A61B 5/015 |

FOREIGN PATENT DOCUMENTS

| | | |
|---|---|---|
| KR | 10-0503424 B1 | 7/2005 |
| KR | 10-2007-0083388 A | 8/2007 |
| KR | 10-1251822 B1 | 4/2013 |
| KR | 10-1768812 B1 | 8/2017 |
| KR | 10-1974786 B1 | 5/2019 |
| KR | 10-2020-0065751 A | 6/2020 |
| KR | 10-2020-0082660 A | 7/2020 |
| KR | 10-2020-0101772 A | 8/2020 |
| KR | 10-2150682 B1 | 9/2020 |

\* cited by examiner ively continued based on the medical image.

METHOD FOR ANALYZING LESION BASED ON MEDICAL IMAGE

CROSS-REFERENCE TO RELATED APPLICATIONS

This application claims priority to and the benefit of Korean Patent Application No. 10-2020-0181634 filed in the Korean Intellectual Property Office on Dec. 23, 2020, the entire contents of which are incorporated herein by reference.

BACKGROUND

Technical Field

The present disclosure relates to a method for processing a medical image, and more particularly, to a method for detecting and evaluating a lesion for a specific disease which exists in a medical image using artificial intelligence.

Description of the Related Art

A medical image is a material that allows physical states of various organs of the human body to be understood. The medical mage includes a digital radiographic image (X-ray), a compute tomography (CT), or magnetic resonance imaging (MRI).

Research and technology development for an automation method for detecting a lesion of a specific disease is steadily continued based on the medical image.

U.S. Pat. No. 7,305,111 (Dec. 4, 2007) discloses a lung nodule detection automation method for lung cancer screening.

BRIEF SUMMARY

The inventors of the present disclosure have identified that some of technologies developed in the related art merely focuses on specifying the lesion which exists in the medical image, and is not capable of generating and processing, and providing information on the lesion in a form suitable for diagnosis of the specific disease. That is, there is a situation in which in terms of providing required information suitable for the diagnosis of the specific disease, the technologies in the related art cannot show a performance which meets a purpose of lesion detection and evaluation.

The inventors of the present disclosure provide various embodiments that improves the shortcomings in the related art. One or more embodiments of the present disclosure provide an improved solution to the technical problems in the related art as well as a solution for the problem identified above by the inventors. Some embodiments provide a method for detecting and evaluating a lesion for diagnosing a specific disease which exists in a medical image.

At least one embodiment of the present disclosure provides a method for analyzing a lesion based on a medical image, which is performed by a computing device. The method may include: obtaining positional information of a suspicious nodule which exists in the medical image; generating a mask for the suspicious nodule based on a patch of the medical image corresponding to the positional information; and determining a class for a state of the suspicious nodule based on the patch of the medical image and the mask for the suspicious nodule.

In an alternative embodiment, the obtaining of the positional information of the suspicious nodule may include generating a probability value for nodule existence of at least one region of interest and candidate positional information included in the medical image by using a pre-trained first model, and determining the positional information of the suspicious nodule from the candidate positional information based on the probability value for the nodule existence of the at least one region of interest by using the pre-trained first model.

In an alternative embodiment, the generating of the mask for the suspicious nodule may include extracting the patch corresponding to the positional information in the medical image, and generating a first mask for the entire region of the suspicious nodule and a second mask for the region representing the specific attribute of the suspicious nodule based on the patch by using the second model.

In an alternative embodiment, the method may further include: generating first numerical information including at least one of a diameter or a volume for the entire region of the suspicious nodule based on the first mask; and generating second numerical information including at least one of a diameter or a volume for the region representing the specific attribute of the suspicious nodule based on the second mask.

In an alternative embodiment, the method may further include calculating an evaluation score for the suspicious nodule based on the class for the state of the suspicious nodule and the first numerical information based on an auxiliary index of diagnosis of a lung disease.

In an alternative embodiment, the method may further include: calculating the evaluation score for the suspicious nodule based on the class for the state of the suspicious nodule, the first numerical information, and the second numerical information based on the auxiliary index of the diagnosis of the lung disease when the class for the state of the suspicious nodule corresponds to a predetermined type for the specific attribute of the suspicious nodule.

In an alternative embodiment, the method may further include generating a user interface based on at least one of the positional information of the suspicious nodule, the mask, the class for the state of the suspicious nodule, the first numerical information, the second numerical information, or the evaluation score.

In an alternative embodiment, the method may further include: checking whether a subject of the medical image and a subject of a pre-analyzed image correspond to each other; and modifying the evaluation score of the medical image or the evaluation score of the pre-analyzed image based on photographing time points of the medical image and the pre-analyzed image by using a pre-trained fourth model when the subject of the medical image and the subject of the pre-analyzed image correspond to each other.

In an alternative embodiment, the modifying of the evaluation score of the medical image or the evaluation score of the pre-analyzed image may include performing registration between the medical image and the pre-analyzed image by using the fourth model, matching the suspicious nodule which exists in the medical image and the suspicious nodule which exists in the pre-analyzed image by using the fourth model, and identifying changed information of the matched suspicious nodule, and modifying the evaluation score of the medical image or the evaluation score of the pre-analyzed image based on the changed information.

In an alternative embodiment, the modifying of the evaluation score of the medical image or the evaluation score of the pre-analyzed image may include modifying the evaluation score of the pre-analyzed image based on the evaluation score of the medical image by using the fourth model when the medical image is photographed at a time point before the pre-analyzed image, and modifying the evaluation score of the medical image based on the evaluation score of the pre-analyzed image by using the fourth model when the medical image is photographed at a time point after the pre-analyzed image.

In an alternative embodiment, the method may further include estimating malignancy score of the suspicious nodule based on the positional information of the suspicious nodule, the class for the state of the suspicious nodule, and the first or second numerical information by using a pre-trained fifth model.

In an alternative embodiment, the method may further include estimating the malignancy score of the suspicious nodule based on the patch and the mask by using a pre-trained fifth model.

In an alternative embodiment, the method may further include generating a user interface based on at least one of the positional information of the suspicious nodule, the mask, the class for the state of the suspicious nodule, the first numerical information, the second numerical information, or the malignancy score.

In an alternative embodiment, the determining of the class for the state of the suspicious nodule may include determining at least one of a type for an attribute of the suspicious nodule, whether speculation is made, or whether calcification is made through different sub models based on the patch and the mask by using a third model including at least one pre-trained sub model.

Another embodiment of the present disclosure provides a method for analyzing a lesion based on a medical image, which is performed by a computing device. The method may include: checking whether a subject of the medical image and a subject of a pre-analyzed image correspond to each other; calculating an evaluation score for a suspicious nodule based on a class for a state of the suspicious nodule and numerical information which exist in the medical image; and modifying the evaluation score of the medical image or the evaluation score of the pre-analyzed image based on photographing time points of the medical image and the pre-analyzed image when the subject of the medical image and the subject of the pre-analyzed image correspond to each other.

In an alternative embodiment, the method may further include storing the evaluation score of the medical image when the subject of the medical image and the subject of the pre-analyzed image do not correspond to each other.

In an alternative embodiment, the method may further include generating a user interface based on the stored evaluation score or the modified evaluation score.

In an alternative embodiment, the modifying of the evaluation score of the medical image or the evaluation score of the pre-analyzed image may include performing registration between the medical image and the pre-analyzed image by using a pre-trained fourth model, matching the suspicious nodule which exists in the medical image and the suspicious nodule which exists in the pre-analyzed image by using the fourth model, and identifying changed information of the matched suspicious nodule, and modifying the evaluation score of the medical image or the evaluation score of the pre-analyzed image based on the changed information.

In an alternative embodiment, the modifying of the evaluation score of the medical image or the evaluation score of the pre-analyzed image may include modifying the evaluation score of the pre-analyzed image based on the evaluation score of the medical image by using a pre-trained fourth model when the medical image is photographed at a time point before the pre-analyzed image, and modifying the evaluation score of the medical image based on the evaluation score of the pre-analyzed image by using the fourth model when the medical image is photographed at a time point after the pre-analyzed image.

Still another embodiment of the present disclosure provides a computer program stored in a computer-readable storage medium. When the computer program is executed by one or more processors, the computer program allows the following operations for analyzing a lesion based on a medical image to be performed, and the operations may include: obtain positional information of a suspicious nodule which exists in the medical image, generate a masks for the suspicious nodule based on a patch of the medical image corresponding to the positional information, and determine a class for a state of the suspicious nodule based on the patch of the medical image and the mask for the suspicious nodule.

Yet another embodiment of the present disclosure provides a computing device analyzing a lesion based on a medical image. The device may include: a processor including at least one core; a memory including program codes executable in the processor; and a network unit receiving a medical image including a thoracic region, and the processor may be configured to obtain positional information of a suspicious nodule which exists in the medical image, generate a mask for the suspicious nodule based on a patch of the medical image corresponding to the positional information, and determine a class for a state of the suspicious nodule based on the patch of the medical image and the mask for the suspicious nodule.

Still yet another embodiment of the present disclosure provides a user terminal providing a user interface. The user terminal may include: a processor including at least one core; a memory; a network unit receiving a user interface based on analysis information of a lesion included in a medical image from a computing device; and an output unit providing the user interface. In this case, the analysis information of the lesion may include at least one of positional information of a suspicious nodule, a mask for the suspicious nodule, a class for a state of the suspicious nodule, numerical information of the suspicious nodule, evaluation information for the suspicious nodule, or malignancy score of the suspicious nodule.

According to an embodiment of the present disclosure, a method for detecting and evaluating a lesion for diagnosing a specific disease which exists in a medical image can be provided.

DETAILED DESCRIPTION

Figure 1:
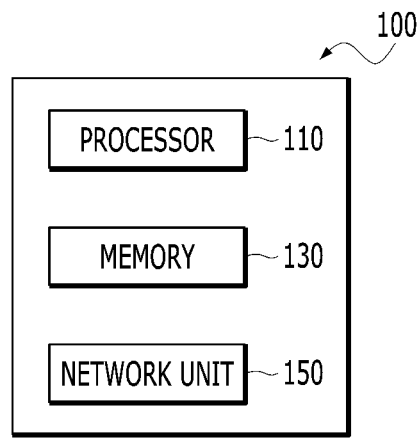
FIG. 1 is a block diagram of a computing device for analyzing a lesion based on a medical image according to an embodiment of the present disclosure.

Hereinafter, various embodiments are described with reference to the drawings. In the present specification, various descriptions are presented for understanding the present disclosure. However, it is obvious that the embodiments may be carried out even without a particular description.

Terms, "component," "module," "system," and the like used in the present specification indicate a computer-related entity, hardware, firmware, software, a combination of software and hardware, or execution of software. For example, a component may be a procedure executed in a processor, a processor, an object, an execution thread, a program, and/or a computer, but is not limited thereto. For example, both an application executed in a computing device and the computing device may be components. One or more components may reside within a processor and/or an execution thread. One component may be localized within one computer. One component may be distributed between two or more computers. Further, the components may be executed by various computer readable medium having various data structures stored therein. For example, components may communicate through local and/or remote processing according to a signal (for example, data transmitted to another system through a network, such as Internet, through data and/or a signal from one component interacting with another component in a local system and a distributed system) having one or more data packets.

A term "or" intends to mean comprehensive "or," not exclusive "or." That is, unless otherwise specified or when it is unclear in context, "X uses A or B" intends to mean one of the natural comprehensive substitutions. That is, when X uses A, X uses B, or X uses both A and B, "X uses A or B" may be applied to any one among the cases. Further, a term "and/or" used in the present specification shall be understood to designate and include all of the possible combinations of one or more items among the listed relevant items.

A term "include" and/or "including" shall be understood as meaning that a corresponding characteristic and/or a constituent element exists. Further, a term "include" and/or "including" means that a corresponding characteristic and/or a constituent element exists, but it shall be understood that the existence or an addition of one or more other characteristics, constituent elements, and/or a group thereof is not excluded. Further, unless otherwise specified or when it is unclear that a single form is indicated in context, the singular shall be construed to generally mean "one or more" in the present specification and the claims.

The term "at least one of A and B" should be interpreted to mean "the case including only A," "the case including only B," and "the case where A and B are combined."

Those skilled in the art shall recognize that the various illustrative logical blocks, configurations, modules, circuits, means, logic, and algorithm operations described in relation to the embodiments additionally disclosed herein may be implemented by electronic hardware, computer software, or in a combination of electronic hardware and computer software. In order to clearly exemplify interchangeability of hardware and software, the various illustrative components, blocks, configurations, means, logic, modules, circuits, and operations have been generally described above in the functional aspects thereof. Whether the functionality is implemented as hardware or software depends on a specific application or design restraints given to the general system. Those skilled in the art may implement the functionality described by various methods for each of the specific applications. However, it shall not be construed that the determinations of the implementation deviate from the range of the contents of the present disclosure.

The description about the presented embodiments is provided so as for those skilled in the art to use or carry out the present disclosure. Various modifications of the embodiments will be apparent to those skilled in the art. General principles defined herein may be applied to other embodiments without departing from the scope of the present disclosure. Therefore, the present disclosure is not limited to the embodiments presented herein. The present disclosure shall be interpreted within the broadest meaning range consistent to the principles and new characteristics presented herein.

In the present specification, a neural network, an artificial neural network, and a network function may often be interchangeably used.

Meanwhile, the term "image" or "image data" used throughout the detailed description and claims of the present disclosure refers to multi-dimensional data constituted by discrete image elements (e.g., pixels in a 2D image), and in other words, refers to an object which may be seen with an eye (e.g., displayed on a video screen) or a digital representation of the object (such as a file corresponding to a pixel output of CT, MRI detector, etc.).

For example, the "image" may be computed tomography (CT), magnetic resonance imaging (MRI), ultrasonic waves, a medical image of a subject collected by any other medical imaging system known in the technical field of the present disclosure. The image may not particularly be provided in a medical context, and may be provided in a non-medical context, and may be for example, a security search X-ray imaging.

Throughout the detailed description and claims of the present disclosure, a 'Digital Imaging and Communications in Medicine (DICOM)' standard is a term which collectively refers to several standards used for digital image representation and communication in a medical device, so that the DICOM standard is announced by the Federation Committee, constituted in the American College Radiology (ACR) and the National Electrical Manufacturers Association (NEMA).

Throughout the detailed description and claims of the present disclosure, a 'Picture Archiving and Communication System (PACS)' is a term that refers to a system for performing storing, processing, and transmitting according to the DICOM standard, and medical images obtained by using digital medical image equipment such as X-ray, CT, and MRI may be stored in a DICOM format and transmitted to terminals inside or outside a hospital through a network, and additionally include a reading result and a medical chart.

FIG. 1 is a block diagram of a computing device for analyzing a lesion based on a medical image according to an embodiment of the present disclosure.

A configuration of the computing device 100 illustrated in FIG. 1 is only an example shown through simplification. In an embodiment of the present disclosure, the computing device 100 may include other components for performing a computing environment of the computing device 100 and only some of the disclosed components may constitute the computing device 100.

The computing device 100 may include a processor 110, a memory 130, and a network unit 150.

The processor 110 may be constituted by one or more cores and may include processors for data analysis and deep learning, which include a central processing unit (CPU), a general purpose graphics processing unit (GPGPU), a tensor processing unit (TPU), and the like of the computing device. The processor 110 may read a computer program stored in the memory 130 to perform data processing for machine learning according to an embodiment of the present disclosure. According to an embodiment of the present disclosure, the processor 110 may perform a calculation for learning the neural network. The processor 110 may perform calculations for learning the neural network, which include processing of input data for learning in deep learning (DL), extracting a feature in the input data, calculating an error, updating a weight of the neural network using backpropagation, and the like. At least one of the CPU, GPGPU, and TPU of the processor 110 may process learning of a network function. For example, both the CPU and the GPGPU may process the learning of the network function and data classification using the network function. Further, in an embodiment of the present disclosure, processors of a plurality of computing devices may be used together to process the learning of the network function and the data classification using the network function. Further, the computer program executed in the computing device according to an embodiment of the present disclosure may be a CPU, GPGPU, or TPU executable program.

According to an embodiment of the present disclosure, the processor 110 may read a lesion for a specific disease based on a medical image by using at least one pre-trained machine learning model. The processor 110 may identify positional information of a lesion which exists in the medical image by inputting the medical image into a detection based neural network model. The processor 110 may generate a patch corresponding to a part of the medical image based on the positional information of the lesion. The processor 110 may generate a mask for the lesion by inputting a patch corresponding to the positional information of the lesion into a segmentation based neural network model. In this case, the mask may mean a data collector including information on an area where the lesion exists in the medical image. The processor 110 may generate class information representing a state of the lesion by inputting the patch and the mask into a classification based neural network model. Through such an operation, the processor 110 may generate information for the lesion (e.g., a location, a state, etc., of the lesion in the human body) which becomes a diagnosis criterion of the specific disease based on the medical image.

For example, the processor 110 may input a medical image including a thoracic region input into the network unit 150 into a pre-trained first model. In this case, the medical image including the thoracic region may include a 3D CT image including at least one lung tissue. The processor 110 inputs, into a first model, the medical image including thoracic region to obtain positional information of a suspicious nodule which exists in the medical image. The positional information of the suspicious nodule may include a center coordinate system of a region in a medical image identified as the suspicious nodule. When the medical image is a 3D CT image, a center coordinate value of a region judged as the suspicious nodule may be included in the positional information of the suspicious nodule.

The processor 110 may extract a patch corresponding to the positional information from the medical image including the thoracic region based on the positional information of the suspicious nodule obtained by using the first model. The processor 110 may input the patch corresponding to the positional information of the suspicious nodule into a pre-trained second model. The processor 110 may generate a mask for the suspicious nodule by inputting the patch generated from the medical image into the second model. In other words, the processor 110 may extract information on a region where the suspicious nodule existing in the patch exists by using the second model.

The processor 110 may input the previously extracted patch into a pre-trained third model together with the mask for the suspicious nodule generated by using the second model. The processor 110 inputs both the mask for the suspicious nodule and the patch into the third model to determine a class regarding a state of the suspicious nodule. In this case, the state of the suspicious nodule may include a feature, an attribute, etc., of the suspicious nodule which becomes a basis of judgment of a lung disease. In other words, the processor 110 may identify in which state the suspicious nodule is within the patch of the medical image by using the third model in order to obtain lesion information for diagnosing the lung disease.

According to an embodiment of the present disclosure, the processor 110 may evaluate a lesion read in the medical image based on an auxiliary index for diagnosing a specific disease. The processor 110 may compute numerical values for the region where the lesion exists based on the mask generated through a segmentation based neural network model. The processor 110 may calculate an evaluation score of the lesion based on numerical information including the numerical values of the lesion and class information for the state of the lesion based on the auxiliary index for diagnosing the specific disease. Further, the processor 110 may also predict malignancy score of the lesion by using the pre-trained neural network model. The processor 110 may estimate the malignancy score of the lesion based on the positional information of the lesion, the class information for the state of the lesion, and the numerical information of the lesion through a regression based neural network model. Through such an operation, the processor 110 may generate evaluation information for the lesion which may be utilized as a diagnosis index of the specific disease based on the medical image.

For example, the processor 110 may generate the numerical information for the region where the suspicious nodule exists within the medical image based on the mask of the suspicious nodule generated by using the second model. In this case, the numerical information may include numerical values regarding a diameter, a volume, etc., of the suspicious nodule. The processor 110 may calculate the evaluation score of the suspicious nodule according to the auxiliary index of lung disease diagnosis stored in the memory 130 based on the numerical information of the suspicious nodule and the class for the state of the suspicious nodule classified by using the third model. In this case, the auxiliary index of the lung disease diagnosis may include a Lung CT Screening Reporting and Data System (Lung-RADS) based classification index, etc. In other words, the processor 110 may determine the evaluation score of the suspicious nodule according to a criterion determined according to the auxiliary index of the lung disease diagnosis by using both structural information and attribute information of the suspicious nodule. The evaluation score determined by the processor 110 may be utilized for lung disease diagnosis and prognosis prediction for a subject of the medical image.

The processor 110 may input, into a pre-trained fifth model, the positional information of the suspicious nodule generated through the first model, the class information for the state of the suspicious nodule generated through the third model, and the numerical information of the suspicious nodule generated based on the mask. The processor 110 may estimate the malignancy score of the suspicious nodule by inputting the positional information, the class information, and the numerical information of the suspicious nodule into the fifth model. Further, the processor 110 may also estimate the malignancy score of the suspicious nodule by inputting the patch extracted from the medical image and the mask generated through the second model into the fifth model. In other words, the processor 110 may also estimate the malignancy score of the suspicious nodule by using quantitative information itself of the suspicious nodule, and also estimate the malignancy score of the suspicious nodule by utilizing image information for the suspicious nodule. The processor 110 may predict the malignancy score of the suspicious nodule which influences the lung disease by simultaneously considering the positional information, the structural information, and the attribute information of the suspicious nodule which exists in the medical image including the thoracic region through the fifth model. The malignancy score predicted by the processor 110 may be utilized for the lung disease diagnosis and the prognosis prediction for the subject of the medical image. According to an embodiment of the present disclosure, the processor 110 may modify the evaluation score for the lesion based on medical images for a specific subject having a time-series relationship by using the pre-trained neural network model. When a medical image for the same subject as a pre-analyzed image is input into the computing device 100 by the processor 110, the processor 110 may determine changed information by matching the pre-analyzed mage and a lesion which exists in a subsequently input medical image by using a pre-trained machine learning model. In addition, the processor 110 may modify the evaluation score by reflecting the changed information to the evaluation score for the lesion. If there is no changed information, the processor 110 may maintain the evaluation score as it is without separate modification of the evaluation score for the lesion.

For example, the processor 110 performs the above-described operations for calculating the evaluation score of the suspicious nodule based on the medical image received through the network unit 150 to store the evaluation score in the memory 130. When receiving a new medical image through the network unit 150, the processor 110 may check whether a subject of the new medical image corresponds to a subject of the pre-analyzed medical images. In other words, the processor 110 may check whether an ID for identifying the subject of the new medical image matches one of IDs of the pre-analyzed medical images. When the identification ID of the new medical image matches one of the identification IDs of the pre-analyzed medical images, the processor 110 may match suspicious nodules which exist a conventional image and a new image by using a pre-trained fourth model. The processor 110 may identify the changed information of the suspicious nodule matched by using the fourth model, and modify the evaluation score for the suspicious nodule based on the changed information. Through such an operation, the processor 110 may effectively track a lesion change of a specific subject, and increase accuracy of information required or prognosis judgment of the lung disease.

According to an embodiment of the present disclosure, the memory 130 may store any type of information generated or determined by the processor 110 and any type of information received by the network unit 150.

According to an embodiment of the present disclosure, the memory 130 may include at least one type of storage medium of a flash memory type storage medium, a hard disk type storage medium, a multimedia card micro type storage medium, a card type memory (for example, an SD or XD memory, or the like), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. The computing device 100 may operate in connection with a web storage performing a storing function of the memory 130 on the Internet. The description of the memory is just an example and the present disclosure is not limited thereto.

The network unit 150 according to an embodiment of the present disclosure may use an arbitrary type known wired/wireless communication systems.

The network unit 150 may receive a medical image representing a physical organ from a medical image photographing system. For example, the medical image representing the physical organ may be training data or inference data of the neural network model trained by a 2D feature or a 3D feature. The medical image representing the physical organ may be a 3D CT region including at least one lung region. The medical image representing the physical organ is not limited to the above-described example, but may include all images related to the physical organ obtained through photographing, such as an X-ray image, an MR image, etc.

The network unit 150 may transmit and receive information processed by the processor 110, a user interface, etc., through communication with the other terminal. For example, the network unit 150 may provide the user interface generated by the processor 110 to a client (e.g., a user terminal). Further, the network unit 150 may receive an external input of a user applied to the client and deliver the received external input to the processor 110. In this case, the processor 110 may process operations such as output, modification, change, addition, etc., of information provided through the user interface based on the external input of the user delivered from the network unit 150.

Meanwhile, according to an embodiment of the present disclosure, the computing device 100 as a computing system that transmits and receives information to and from the client through communication may include a server. In this case, the client may be any type of terminal which may access the server. For example, the computing device 100 which is the server may receive the medical image from the medical image photographing system and analyze the lesion, and provide a user interface including an analysis result to the user terminal. In this case, the user terminal may output the user interface received from the computing device 100 as the server, and receive and process the information through an interaction with the user.

The user terminal may display the user interface provided to provide analysis information of the lesion (e.g., the suspicious nodule, etc.) included in the medical image delivered from the computing device 100 which is the server. Although not separately illustrated, the user terminal may include a network unit receiving the user interface from the computing device 100, a processor including at least one core, a memory, an output unit providing the user interface, and an input unit receiving the external input applied from the user.

In an additional embodiment, the computing device 100 may also include any type of terminal that performs additional information processing by receiving a data resource generated in any server.

Figure 2:
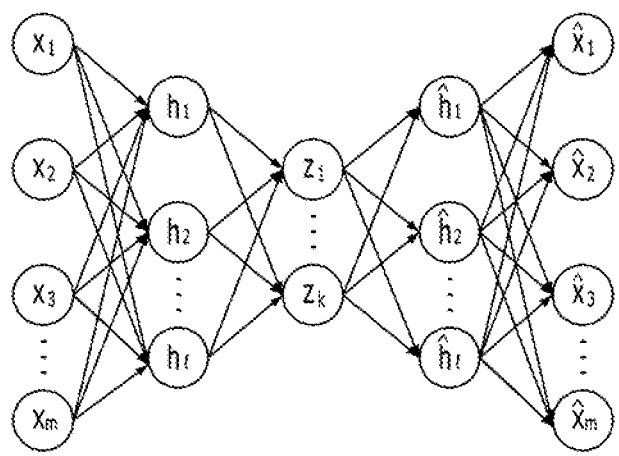
FIG. 2 is a schematic diagram illustrating a network function according to an embodiment of the present disclosure.

FIG. 2 is a schematic diagram illustrating a network function according to an embodiment of the present disclosure.

Throughout the present disclosure, a model, a computation model, the neural network, a network function, and the neural network may be used as an interchangeable meaning. The neural network may be generally constituted by an aggregate of calculation units which are mutually connected to each other, which may be called nodes. The nodes may also be called neurons. The neural network is configured to include one or more nodes. The nodes (alternatively, neurons) constituting the neural networks may be connected to each other by one or more links.

In the neural network, one or more nodes connected through the link may relatively form the relationship between an input node and an output node. Concepts of the input node and the output node are relative and a predetermined node which has the output node relationship with respect to one node may have the input node relationship in the relationship with another node and vice versa. As described above, the relationship of the input node to the output node may be generated based on the link. One or more output nodes may be connected to one input node through the link and vice versa.

In the relationship of the input node and the output node connected through one link, a value of data of the output node may be determined based on data input in the input node. Here, a link connecting the input node and the output node to each other may have a weight. The weight may be variable and the weight is variable by a user or an algorithm in order for the neural network to perform a desired function. For example, when one or more input nodes are mutually connected to one output node by the respective links, the output node may determine an output node value based on values input in the input nodes connected with the output node and the weights set in the links corresponding to the respective input nodes.

As described above, in the neural network, one or more nodes are connected to each other through one or more links to form a relationship of the input node and output node in the neural network. A characteristic of the neural network may be determined according to the number of nodes, the number of links, correlations between the nodes and the links, and values of the weights granted to the respective links in the neural network. For example, when the same number of nodes and links exist and there are two neural networks in which the weight values of the links are different from each other, it may be recognized that two neural networks are different from each other.

The neural network may be constituted by a set of one or more nodes. A subset of the nodes constituting the neural network may constitute a layer. Some of the nodes constituting the neural network may constitute one layer based on the distances from the initial input node. For example, a set of nodes of which distance from the initial input node is n may constitute n layers. The distance from the initial input node may be defined by the minimum number of links which should be passed through for reaching the corresponding node from the initial input node. However, definition of the layer is predetermined for description and the order of the layer in the neural network may be defined by a method different from the aforementioned method. For example, the layers of the nodes may be defined by the distance from a final output node.

The initial input node may mean one or more nodes in which data is directly input without passing through the links in the relationships with other nodes among the nodes in the neural network. Alternatively, in the neural network, in the relationship between the nodes based on the link, the initial input node may mean nodes which do not have other input nodes connected through the links. Similarly thereto, the final output node may mean one or more nodes which do not have the output node in the relationship with other nodes among the nodes in the neural network. Further, a hidden node may mean nodes constituting the neural network other than the initial input node and the final output node.

In the neural network according to an embodiment of the present disclosure, the number of nodes of the input layer may be the same as the number of nodes of the output layer, and the neural network may be a neural network of a type in which the number of nodes decreases and then, increases again from the input layer to the hidden layer. Further, in the neural network according to another embodiment of the present disclosure, the number of nodes of the input layer may be smaller than the number of nodes of the output layer, and the neural network may be a neural network of a type in which the number of nodes decreases from the input layer to the hidden layer. Further, in the neural network according to yet another embodiment of the present disclosure, the number of nodes of the input layer may be larger than the number of nodes of the output layer, and the neural network may be a neural network of a type in which the number of nodes increases from the input layer to the hidden layer. The neural network according to still yet another embodiment of the present disclosure may be a neural network of a type in which the neural networks are combined.

A deep neural network (DNN) may refer to a neural network that includes a plurality of hidden layers in addition to the input and output layers. When the deep neural network is used, the latent structures of data may be determined. That is, latent structures of photos, text, video, voice, and music (e.g., what objects are in the photo, what the content and feelings of the text are, what the content and feelings of the voice are) may be determined. The deep neural network may include a convolutional neural network (CNN), a recurrent neural network (RNN), an auto encoder, generative adversarial networks (GAN), a restricted Boltzmann machine (RBM), a deep belief network (DBN), a Q network, a U network, a Siam network, a Generative Adversarial Network (GAN), and the like. The description of the deep neural network described above is just an example and the present disclosure is not limited thereto.

In an embodiment of the present disclosure, the network function may include the auto encoder. The auto encoder may be a kind of artificial neural network for outputting output data similar to input data. The auto encoder may include at least one hidden layer and odd hidden layers may be disposed between the input and output layers. The number of nodes in each layer may be reduced from the number of nodes in the input layer to an intermediate layer called a bottleneck layer (encoding), and then expanded symmetrical to reduction to the output layer (symmetrical to the input layer) in the bottleneck layer. The auto encoder may perform non-linear dimensional reduction. The number of input and output layers may correspond to a dimension after preprocessing the input data. The auto encoder structure may have a structure in which the number of nodes in the hidden layer included in the encoder decreases as a distance from the input layer increases. When the number of nodes in the bottleneck layer (a layer having a smallest number of nodes positioned between an encoder and a decoder) is too small, a sufficient amount of information may not be delivered, and as a result, the number of nodes in the bottleneck layer may be maintained to be a specific number or more (e.g., half of the input layers or more).

The neural network may be learned in at least one scheme of supervised learning, unsupervised learning, semi-supervised learning, or reinforcement learning. The learning of the neural network may be a process in which the neural network applies knowledge for performing a specific operation to the neural network.

The neural network may be learned in a direction to reduce or minimize errors of an output. The learning of the neural network is a process of repeatedly inputting learning data into the neural network and calculating the output of the neural network for the learning data and the error of a target and back-propagating the errors of the neural network from the output layer of the neural network toward the input layer in a direction to reduce the errors to update the weight of each node of the neural network. In the case of the supervised learning, the learning data labeled with a correct answer is used for each learning data (i.e., the labeled learning data) and in the case of the unsupervised learning, the correct answer may not be labeled in each learning data. That is, for example, the learning data in the case of the supervised learning related to the data classification may be data in which category is labeled in each learning data. The labeled learning data is input to the neural network, and the error may be calculated by comparing the output (category) of the neural network with the label of the learning data. As another example, in the case of the unsupervised learning related to the data classification, the learning data as the input is compared with the output of the neural network to calculate the error. The calculated error is back-propagated in a reverse direction (i.e., a direction from the output layer toward the input layer) in the neural network and connection weights of respective nodes of each layer of the neural network may be updated according to the back propagation. A variation amount of the updated connection weight of each node may be determined according to a learning rate. Calculation of the neural network for the input data and the back-propagation of the error may constitute a learning cycle (epoch). The learning rate may be applied differently according to the number of repetition times of the learning cycle of the neural network. For example, in an initial stage of the learning of the neural network, the neural network ensures a certain level of performance quickly by using a high learning rate, thereby increasing efficiency and uses a low learning rate in a latter stage of the learning, thereby increasing accuracy.

In learning of the neural network, the learning data may be generally a subset of actual data (i.e., data to be processed using the learned neural network), and as a result, there may be a learning cycle in which errors for the learning data decrease, but the errors for the actual data increase. Overfitting is a phenomenon in which the errors for the actual data increase due to excessive learning of the learning data. For example, a phenomenon in which the neural network that learns a cat by showing a yellow cat sees a cat other than the yellow cat and does not recognize the corresponding cat as the cat may be a kind of overfitting. The overfitting may act as a cause which increases the error of the machine learning algorithm. Various optimization methods may be used in order to prevent the overfitting. In order to prevent the overfitting, a method such as increasing the learning data, regularization, dropout of omitting a part of the node of the network in the process of learning, utilization of a batch normalization layer, etc., may be applied.

Figure 3:
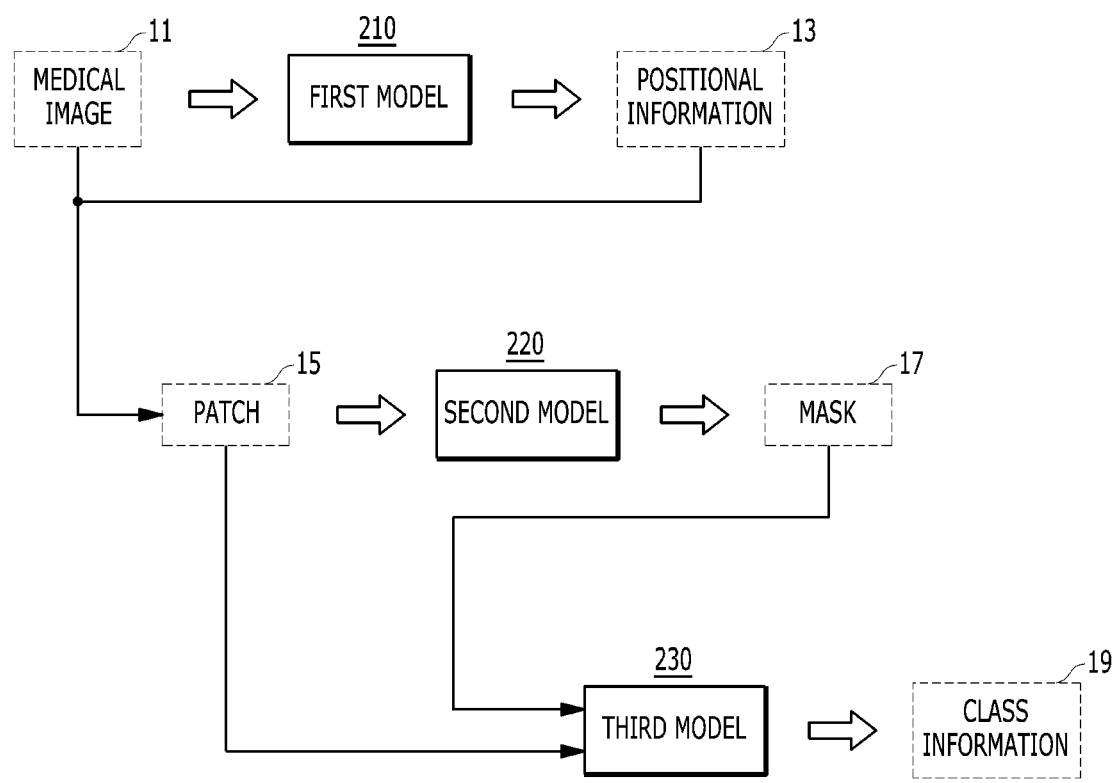
FIG. 3 is a block diagram illustrating a process of reading a lesion of a computing device according to an embodiment of the present disclosure.

FIG. 3 is a block diagram illustrating a process of reading a lesion of a computing device according to an embodiment of the present disclosure.

Referring to FIG. 3, the processor 110 of the computing device 100 according to an embodiment of the present disclosure may obtain positional information 13 of a suspicious nodule existing in a medical image 11 by using a pre-trained first model 210. For example, the processor 110 inputs the medical image 11 into the first model 210 to generate a probability value for existence of a nodule in at least one region of interest, and candidate positional information included in the medical image 11. Here, the region of interest may mean one region in the medical image corresponding to a candidate group of the suspicious nodule. Further, the candidate positional information may mean positional information of the region of interest. The processor 110 may determine the positional information 13 of the suspicious nodule based on the probability value for the nodule existence in at least one region of interest by using the first model 210. The processor 110 may check whether each probability value for the nodule existence of the regions of interest is equal to or more than a predetermined threshold. The processor 110 may determine positional information of at least one region of interest corresponding to the probability value which is equal to or more than the predetermined threshold as the positional information 13 of the suspicious nodule.

The processor 110 may extracted a patch 15 corresponding to input data of a pre-trained second model 220 or third model 230 from the medical image 11 based on the positional information 13 of the suspicious nodule. In other words, the processor 110 extracts a region corresponding to the positional information 13 of the suspicious nodule in the medical image 11 to generate the patch 15. Accordingly, the patch 15 may be image data including meaningful information for the suspicious nodule by filtering a region not required for lesion analysis in the medical image. The processor 110 may generate a mask 17 for the suspicious nodule based on the patch 15 by using the second model 220. For example, the processor 110 inputs the patch 15 into the second model 220 to generate the mask 17 for at least one of an entire region of the suspicious nodule or a region representing a specific attribute of the suspicious nodule. In this case, the specific attribute as one of the attribute types representing in which state the suspicious nodule is may be a solid attribute, but this is just one example, and is not limited to the above-described example. The processor 110 may remove information not required from the medical image 11 and effectively extract information on the region where the suspicious nodule exists through the operation using the second model 220.

The processor 110 may generate class information 19 for the state of the suspicious nodule based on the patch 15 and the mask 17 corresponding to the output of the second model 220 by using the pre-trained third model 230. The third model 230 may output more accurate class information 19 than a case of receiving only the patch 15 by receiving both the patch 15 and the mask 17. For example, the processor 110 inputs both the patch 15 and the mask 17 into the third model 230 including at least one sub model to generate the class information 19 representing at least one of a type for the attribute of the suspicious nodule, whether speculation is made, or whether calcification is made through different sub models. Specifically, the processor 110 may determine the type for the solid attribute of the suspicious nodule based on the patch 15, and the mask for the entire region of the suspicious nodule and the mask for the region representing the specific attribute of the suspicious nodule by using a first sub model of the third model 230. The processor 110 may determine whether the suspicious nodule is speculated based on the patch 15, and the mask for the entire region of the suspicious nodule and the mask for the region representing the specific attribute of the suspicious nodule by using a second sub model of the third model 230. The processor 110 may determine whether the suspicious nodule is calcified based on the patch 15, and the mask for the entire region of the suspicious nodule and the mask for the region representing the specific attribute of the suspicious nodule by using a third sub model of the third model 230. A plurality of sub models included in the third model 230 may also perform a parallel operation for each type of class as described above, but the third model 230 which is a single model may also perform an operation of autonomously determining various types of classes. Further, the third model 230 may also include all of three sub models described above and also include only some thereof.

Figure 4:
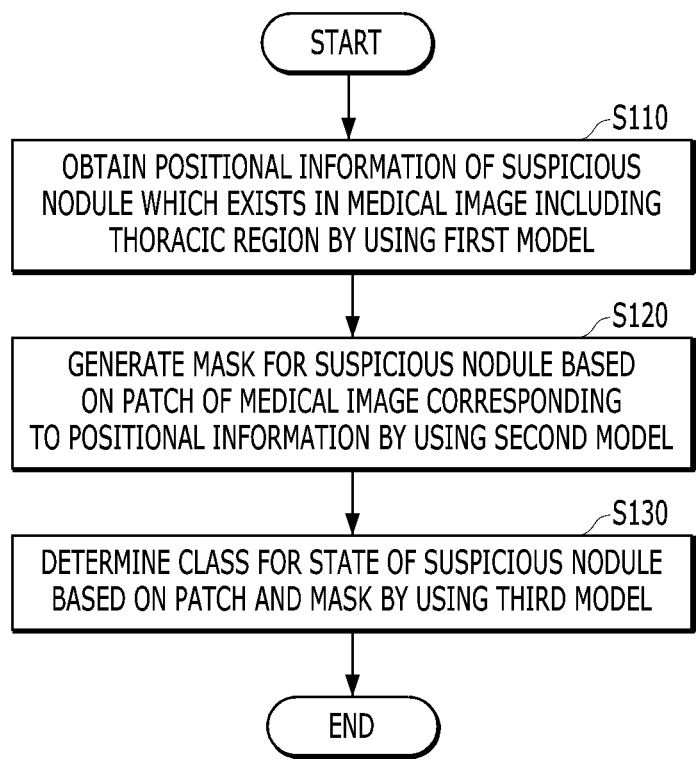
FIG. 4 is a flowchart illustrating a process of reading a lesion of a computing device according to an embodiment of the present disclosure.

FIG. 4 is a flowchart illustrating a process of reading a lesion of a computing device according to an embodiment of the present disclosure.

Referring to FIG. 4, in step S110, a computing device 100 may receive medical images obtained by photographing a physical organ corresponding to a lesion analysis subject from a medical image photographing system. For example, the medical image may be a CT image obtained by photographing a thoracic region to include a lung. The computing device 100 may obtain positional information of a lesion which exists in the medical image by using a first model which is a pre-trained neural network model. For example, the computing device 100 may obtain a center coordinate value of the suspicious nodule in the CT image obtained by photographing the thoracic region by using the first model.

In step S120, the computing device 100 may extract an image unit having a predetermined specification in the medical image based on the positional information of the lesion. The predetermined specification may be optimized according to an input of the pre-trained neural network model. For example, the computing device 100 may obtain the patch centering on the center coordinate value of the suspicious nodule obtain through the first model. The computing device 100 may generate the mask for the lesion based on the image unit extracted from the medical image by using a second model which is the pre-trained neural network model. For example, the computing device 100 inputs the patch corresponding to the center coordinate value of the suspicious nodule into the second model to generate a mask including information on the suspicious nodule.

In step S130, the computing device 100 may determine the class for the state of the lesion based on the image unit extracted in step S120 and the mask by using a third model which is the pre-trained neural network model. For example, the computing device 100 may determine the class for the state of the suspicious nodule by inputting the patch corresponding to the center coordinate value of the suspicious nodule and the mask generated through the second model into the third model. In this case, the state of the suspicious nodule may represent a physical attribute of the suspicious nodule (e.g., a solid, a partial-solid, a non-solid, etc.) and characteristics (e.g., speculation, calcification, etc.).

Figure 5:
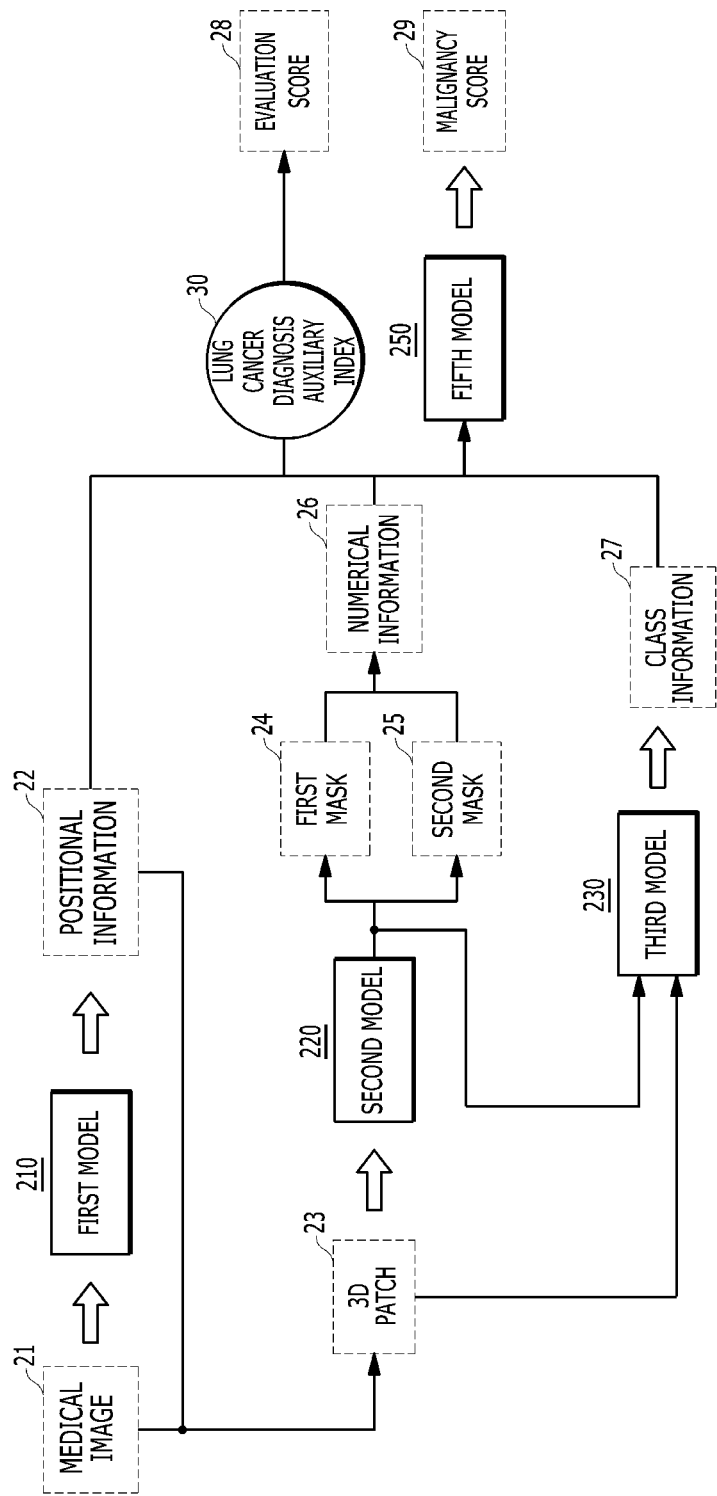
FIG. 5 is a block diagram illustrating a process of reading and evaluating a lesion of a computing device according to an embodiment of the present disclosure.

FIG. 5 is a block diagram illustrating a process of reading and evaluating a lesion of a computing device according to an embodiment of the present disclosure.

Referring to FIG. 5, the processor 110 of the computing device 100 according to an embodiment of the present disclosure inputs the medical image 21 including at least one lung region into the first model 210 to generate the positional information 22 of the suspicious nodule which exists in the lung region. The processor 110 inputs a 3D patch 23 extracted from the medical image 21 into the second model 220 based on the positional information 22 of the suspicious nodule to generate a plurality of masks 24 and 25. In this case, a first mask 24 may be a mask including information on an entire region of the suspicious nodule. A second mask 25 may be a mask including information on a region where the suspicious nodule represents the specific attribute (e.g., solid, etc.) in the entire region of the suspicious nodule. The processor 110 inputs the 3D patch 23 and the plurality of masks 24 and 25 into the third model 230 to generate class information 27 representing the type of attribute of the suspicious nodule, whether the suspicious nodule is speculated, whether the suspicious nodule is calcified, etc.

Meanwhile, the processor 110 may generate numerical information 26 including at least one of a diameter and a volume of the suspicious nodule based on the masks 24 and 25 for the suspicious nodule. In this case, the numerical information 26 includes first numerical information generated based on the first mask 24, but may additionally include second numerical information generated based on the second mask 25 according to a specific class of the suspicious nodule. The first numerical information may include a numerical value representing at least one of a diameter or a volume for the entire region of the suspicious nodule which exists in the medical image 21. The second numerical information may include a numerical value representing at least one of a diameter or a volume for the region representing the specific attribute of the suspicious nodule which exists in the medical image 21. The processor 110 may calculate structural numerical values related to a shape, a size, etc., of a region corresponding to the suspicious nodule within the 3D patch 23 based on information included in the first mask 24. However, when the class for the state of the suspicious nodule corresponds to a predetermined type (e.g., partial-solid) for the specific attribute of the suspicious nodule, the processor 110 may calculate the above-described numerical values based on information included in the second mask 25 together with the information included in the first mask 24.

The processor 110 may calculate an evaluation score 28 of the suspicious nodule based on the numerical information 26 and the class information 27 based on the auxiliary index 30 of diagnosis of the lung disease. For example, the processor 110 may evaluate the suspicious nodule by one of scores specified by the auxiliary index 30 by reviewing the numerical information 26 and the class information 27 of the suspicious nodule detected from the medical image 21 based on the auxiliary index 30 of diagnosis of a lung cancer. Specifically, the processor 110 may check in which category of six lung-RADS classification categories the suspicious nodule is included based the numerical value for a diameter, a volume, etc., of at least one of the entire region of the suspicious nodule or the region representing the solid attribute, which is included in the numerical information 26 and information on the type of the solid attribute, whether the spiculation is made, or whether the calcification is made, which is included in the class information 27. When the type for the solid attribute of the suspicious nodule on the class information 27 is the solid or the non-solid, the processor 110 may check to which category of the lung-RADS classification categories the suspicious nodule belongs by using the first numerical information included in the numerical information 26. When the type for the solid attribute of the suspicious nodule on the class information 27 is the partial-solid, the processor 110 may check to which category of the lung-RADS classification categories the suspicious nodule belongs by using both the first numerical information and the second numerical information included in the numerical information 26. The processor 110 may determine one of six lung-RADS classification categories by the evaluation score 28 of the suspicious nodule based on a result of the judgment.

The processor 110 may predict a degree at which the suspicious nodule influences the lung as a cause of the lung disease based on information on the suspicious nodule output through the first model 210, the second model 220, and the third model 230. The processor 110 may estimate malignancy score 29 of the suspicious nodule based on the positional information 22, the numerical information 26, and the class information 27 of the suspicious nodule by using the pre-trained fifth model 250. For example, the processor 110 inputs a center coordinate value of the nodule included in the positional information 22, a size value of the nodule included in the numerical information 26, and information on the type of the solid attribute, whether the speculation is made, or whether the calcification is made, etc., included in the class information 27 into the fifth model 250 to calculate the malignancy score 29 of the suspicious nodule.

Although not illustrated in FIG. 5, the processor 110 may also estimate the malignancy score 29 of the suspicious nodule based on the 3D patch 23 extracted from the medical image 21 by using the pre-trained fifth model 250 and the masks 24 and 25 generated through the second model 220. That is, the processor 110 may also estimate the malignancy score 29 by directly inputting quantitative information 22, 26, and 27 for the suspicious nodule extracted from the medical image 21 into the fifth model 250, and estimate the malignancy score 29 by inputting image information 23, 24, and 25 generated through processing the medical image 21 into the fifth model.

Figure 6:
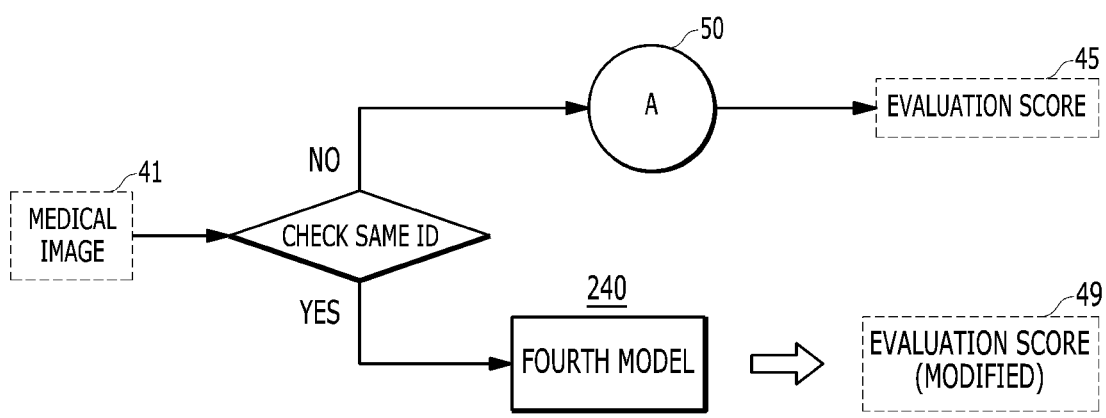
FIG. 6 is a block diagram illustrating a process of modifying an evaluation result of a lesion of a computing device according to an embodiment of the present disclosure.

FIG. 6 is a block diagram illustrating a process of modifying an evaluation result of a lesion of a computing device according to an embodiment of the present disclosure.

Referring to FIG. 6, the processor 110 of the computing device 100 according to an embodiment of the present disclosure may modify the evaluation score for the suspicious nodule based on time-series medical images of the same subject. The processor 110 may modify the evaluation score for the suspicious nodule based on a photographing time point of the time-series medical images of the same subject. When the medical images are sequentially input into the computing device 100, the processor 110 may check whether a history analyzed by inputting an image targeting the same subject as the medical image 41 exists. When it is judged that there is no history for the image targeting the same subject as the medical image 41, the processor 110 may recognize the medical image 41 as a medical image for a new subject, and calculate the evaluation score 45 for the suspicious nodule through step A (50). In this case, it may be appreciated that step A (50) corresponds to a calculation process of the evaluation score 28 illustrated in FIG. 5.

When it is judged that there is a pre-analyzed image targeting the same subject as the medical image 41, the processor 110 may perform registration between the pre-analyzed image and the medical image 41 by using the pre-trained fourth model 240. Here, the registration means an operation of adjusting a relative positional relationship between the pre-analyzed image and the medical image 41 having a time difference. The processor 110 may match a suspicious nodule which exists in the pre-analyzed image of which registration is completed and the suspicious nodule which exits in the medical image 41 by using the fourth model 240. Although not illustrated in FIG. 6, the processor 110 may identify changed information between the suspicious nodules matched by performing step A (50) for the medical image 41. In this case, it may be appreciated that step A (50) corresponds to a calculation process of the evaluation score 28 illustrated in FIG. 5. The processor 110 may modify the evaluation score of the medical image 41 or the evaluation score of the pre-analyzed image based on the changed information. When the medical image 41 is photographed at a time point before the pre-analyzed image, the processor 110 may modify the evaluation score of the pre-analyzed image based on the changed information. On the contrary, when the medical image 41 is photographed at a time point after the pre-analyzed image, the processor 110 may modify the evaluation score of the medical image based on the changed information. That is, the processor 110 compares photographing times points of the medical image 41 and the pre-analyzed image to modify an evaluation score of an image photographed at a most recent time point. In other words, the processor 110 may modify the evaluation score for the image photographed at the most recent time point in order to effectively track a temporal change of the suspicious nodule. Through such a process, the processor 110 may finally generate a modified evaluation score 49 of the suspicious nodule for a specific subject. Such a modification operation of the evaluation score may be repeatedly performed whenever the medical image 41 is input into the computing device 100.

Figure 7:
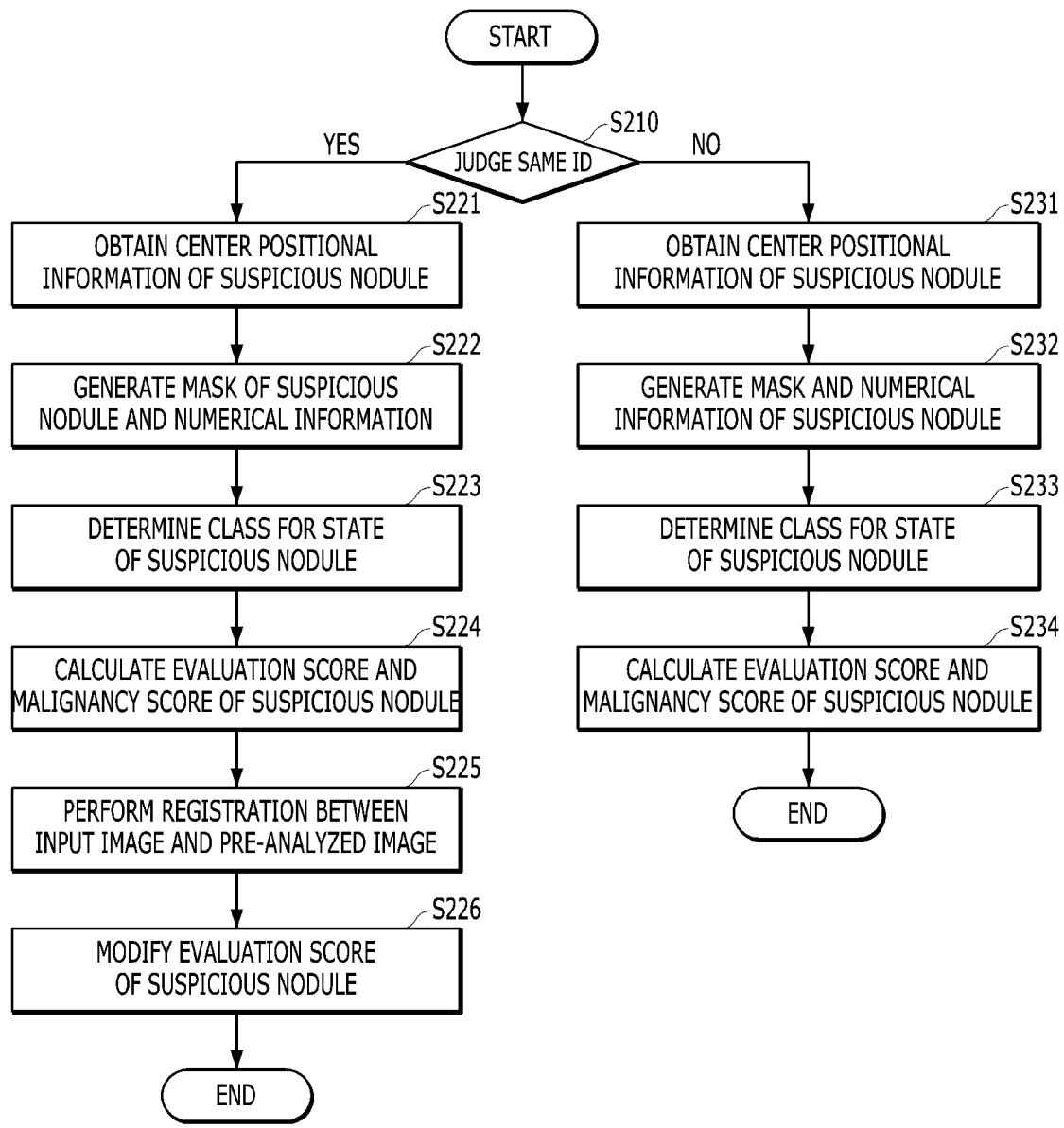
FIG. 7 is a flowchart of a method for analyzing a lesion based on a medical image according to an embodiment of the present disclosure.

FIG. 7 is a flowchart of a method for analyzing a lesion based on a medical image according to an embodiment of the present disclosure.

Referring to FIG. 7, in step S210, when a medical image including a thoracic region is input, a computing device 100 according to an embodiment of the present disclosure may check whether an image having the same ID as an input image exists among pre-analyzed images. Here, the ID represents identification information for a photographing target of the image. For example, the computing device 100 may check whether a subject of an input CT image corresponds to a subject of an already analyzed CT image. When the subject of the input CT image corresponds to the subject of the already analyzed CT image, the computing device 100 may perform a series of operations for modifying an evaluation score of a suspicious nodule which is pre-calculated and stored. When the subject of the input CT image does not correspond to the subject of the already analyzed CT image, the computing device 100 may perform a series of operations for regarding that the medical image for the new subject is input, and reading and evaluating the suspicious nodule based on the input CT image.

Hereinafter, a process for modifying the evaluation score of the suspicious nodule performed by judging that the subjects of the input image and the conventional image correspond to each other will be generally described.

In step S221, the computing device 100 may obtain center positional information of the suspicious nodule which exists in a lung tissue based on the input image. For example, the computing device 100 may generate information on a candidate region of at least one suspicious nodule based on the input image by using a pre-trained detection based neural network model. The computing device 100 may generate the center positional information of the suspicious nodule based on the information on the candidate region by using the detection based neural network model.

In step S222, the computing device 100 may extract an image patch based on the center positional information of the suspicious nodule from the input image. The computing device 100 may generate a mask of the suspicious nodule based on the image patch extracted from the input image. The computing device 100 may generate numerical information including structural numerical values of the suspicious nodule based on the mask of the suspicious nodule. For example, the computing device 100 may generate a plurality of masks for the suspicious nodule based on the image patch by using a pre-trained segmentation based neural network model. The computing device 100 may generate numerical information by computing numerical values related to a diameter, a volume, etc., of the suspicious nodule based on information included in the plurality of masks. In this case, the numerical information may include at least one of first numerical information including structural information for an entire region of the suspicious nodule or second numerical information including structural information for a region representing a specific attribute (e.g., a solid attribute) of the suspicious nodule.

In step S223, the computing device 100 may determine a class for a state of the suspicious nodule based on the image patch and the mask generated in step S222. The class for the state of the suspicious nodule may include a first class representing a type regarding an attribute of the suspicious nodule, a second class representing whether the suspicious nodule is speculated, and a third class representing whether the suspicious nodule is calcified. The computing device 100 may classify the state of the suspicious nodule into each of the first class, the second class, and the third class. For example, the computing device 100 may classify a type for a solid attribute of the suspicious nodule into a solid, a partial-solid, or a non-solid based on the image patch and the plurality of masks by using a first sub model of a pre-trained classification based neural network model. The computing device 100 may classify the suspicious nodule into speculation or non-speculation based on the image patch and the plurality of masks by using a second sub model of the classification based neural network model. The computing device 100 may classify the suspicious nodule into calcification or non-calcification based on the image patch and the plurality of masks by using a third sub model of the classification based neural network model.

In step S224, the computing device 100 may calculate the evaluation score and the malignancy score of the suspicious nodule based on the center positional information of the suspicious nodule generated in step S221, the numerical information generated in step S222, and the class information generated in step S223. For example, the computing device 100 may derive the evaluation score of the suspicious nodule by computing the numerical information and the class information according to a criterion specified in a predetermined diagnosis auxiliary index. The computing device 100 may estimate the malignancy score of the suspicious nodule based on the center positional information, the numerical information, and the class information of the suspicious nodule by using a pre-trained regression based neural network model. Further, the computing device 100 may also estimate the malignancy score of the suspicious nodule based on the image patch and the mask generated in step S222 by using the pre-trained regression based neural network model.

In step S225, the computing device 100 may perform registration that matches relative locations of the input image and the conventional image. The computing device 10 may determine a change of the suspicious nodule by matching the suspicious nodule of the input image read through the above-described steps, and the suspicious nodule of the conventional image which is pre-read and stored. For example, the computing device 100 may perform the registration between the input image and the conventional image by using a pre-trained machine learning model. The computing device 100 may check whether a change between the matched suspicious nodules occurs by matching at least one suspicious nodule which exists in each of two images of which registration is completed.

In step S226, when it is judged that the change occurs in the suspicious nodules matched between the input image and the conventional image, the computing device 100 may calculate a modified evaluation score by reflecting the evaluation score of the suspicious nodule derived from the input image or the evaluation score of the suspicious nodule derived from the conventional image to a mutual evaluation score. In this case, an image subject in which the evaluation score is modified may be determined based on a photographing time point of the image. For example, when the input image is a 2009-year photographing image of a specific subject and the conventional image is a 2015-year photographing image of the specific subject, the computing device 100 may modify the evaluation score of the conventional image by reflecting the evaluation score of the input image to the evaluation score of the conventional image. On the contrary, when the input image is the 2015-year photographing image of the specific subject and the conventional image is the 2009-year photographing image of the specific subject, the computing device 100 may modify the evaluation score of the input image by reflecting the evaluation score of the conventional image to the evaluation score of the input image. When it is judged that the change does not occur in the suspicious nodules matched between the input image and the conventional image, the computing device 100 may maintain the conventional evaluation score without modifying the conventional evaluation score.

Meanwhile, since steps S231 to S234 regarding the process of reading and evaluating the suspicious nodule performed by judging that the subjects of the input image and the conventional image do not correspond to each other correspond to steps S221 to S224 described above, a detailed description will be omitted.

Figure 8:
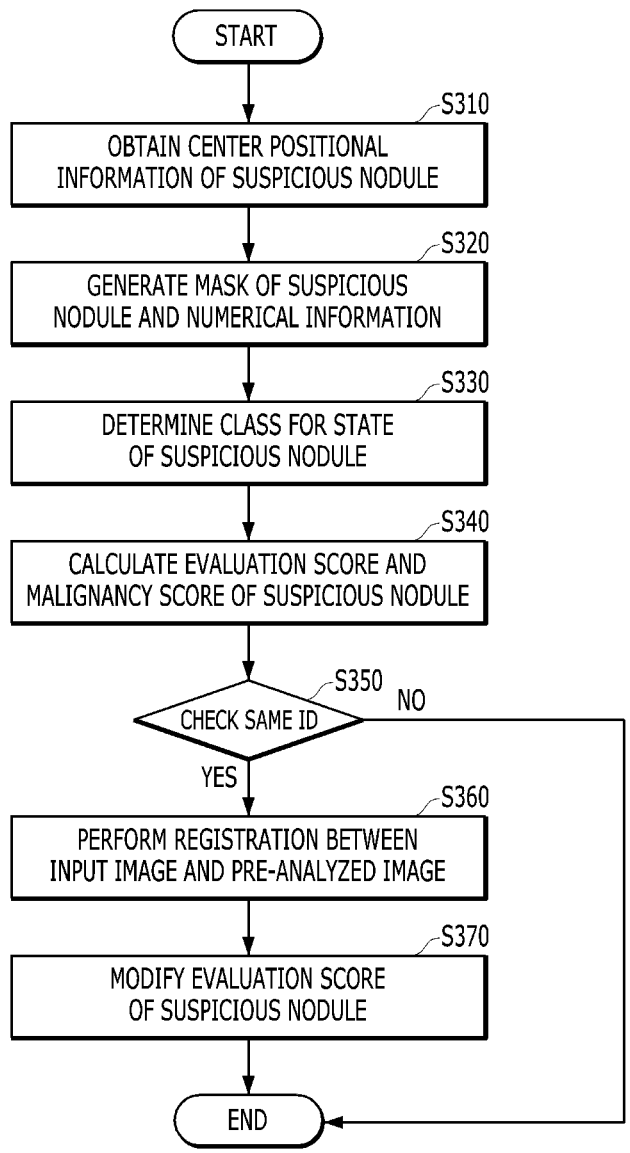
FIG. 8 is a flowchart of a method for analyzing a lesion based on a medical image according to an embodiment of the present disclosure.

FIG. 8 is a flowchart of a method for analyzing a lesion based on a medical image according to an embodiment of the present disclosure.

Referring to FIG. 8, when a medical image including a thoracic region is input, a computing device 100 according to an alternative embodiment of the present disclosure may perform reading and evaluation for a suspicious nodule. Unlike FIG. 7, in FIG. 8, after performing the reading and the evaluation for the suspicious nodule, it is checked whether the input image is an image photographed based on the same subject as the conventional image. That is, it may be appreciated that the method illustrated in FIG. 7 and the method illustrated in FIG. 8 are different in terms of an order relationship of judgment for modifying the evaluation score of the suspicious nodule. Accordingly, a description of contents corresponding to FIG. 7 in relation to detailed contents of respective steps (steps S310 to S370) of FIG. 8 will be omitted.

In the meantime, according to an embodiment of the present disclosure, a computer readable medium storing a data structure is disclosed.

The data structure may refer to organization, management, and storage of data that enable efficient access and modification of data. The data structure may refer to organization of data for solving a specific problem (for example, data search, data storage, and data modification in the shortest time). The data structure may also be defined with a physical or logical relationship between the data elements designed to support a specific data processing function. A logical relationship between data elements may include a connection relationship between user defined data elements. A physical relationship between data elements may include an actual relationship between the data elements physically stored in a computer readable storage medium (for example, a permanent storage device). In particular, the data structure may include a set of data, a relationship between data, and a function or a command applicable to data. Through the effectively designed data structure, the computing device may perform a calculation while minimally using resources of the computing device. In particular, the computing device may improve efficiency of calculation, reading, insertion, deletion, comparison, exchange, and search through the effectively designed data structure.

The data structure may be divided into a linear data structure and a non-linear data structure according to the form of the data structure. The linear data structure may be the structure in which only one data is connected after one data. The linear data structure may include a list, a stack, a queue, and a deque. The list may mean a series of dataset in which order exists internally. The list may include a linked list. The linked list may have a data structure in which data is connected in a method in which each data has a pointer and is linked in a single line. In the linked list, the pointer may include information about the connection with the next or previous data. The linked list may be expressed as a single linked list, a double linked list, and a circular linked list according to the form. The stack may have a data listing structure with limited access to data. The stack may have a linear data structure that may process (for example, insert or delete) data only at one end of the data structure. The data stored in the stack may have a data structure (Last In First Out, LIFO) in which the later the data enters, the sooner the data comes out. The queue is a data listing structure with limited access to data, and may have a data structure (First In First Out, FIFO) in which the later the data is stored, the later the data comes out, unlike the stack. The deque may have a data structure that may process data at both ends of the data structure.

The non-linear data structure may be the structure in which the plurality of pieces of data is connected after one data. The non-linear data structure may include a graph data structure. The graph data structure may be defined with a vertex and an edge, and the edge may include a line connecting two different vertexes. The graph data structure may include a tree data structure. The tree data structure may be the data structure in which a path connecting two different vertexes among the plurality of vertexes included in the tree is one. That is, the tree data structure may be the data structure in which a loop is not formed in the graph data structure.

Throughout the present specification, a calculation model, a nerve network, the network function, and the neural network may be used with the same meaning. Hereinafter, the terms of the calculation model, the nerve network, the network function, and the neural network are unified and described with a neural network. The data structure may include a neural network. Further, the data structure including the neural network may be stored in a computer readable medium. The data structure including the neural network may also include preprocessed data for processing by the neural network, data input to the neural network, a weight of the neural network, a hyper-parameter of the neural network, data obtained from the neural network, an active function associated with each node or layer of the neural network, and a loss function for training of the neural network. The data structure including the neural network may include predetermined configuration elements among the disclosed configurations. That is, the data structure including the neural network may include the entirety or a predetermined combination of pre-processed data for processing by neural network, data input to the neural network, a weight of the neural network, a hyper parameter of the neural network, data obtained from the neural network, an active function associated with each node or layer of the neural network, and a loss function for training the neural network. In addition to the foregoing configurations, the data structure including the neural network may include predetermined other information determining a characteristic of the neural network. Further, the data structure may include all type of data used or generated in a computation process of the neural network, and is not limited to the foregoing matter. The computer readable medium may include a computer readable recording medium and/or a computer readable transmission medium. The neural network may be formed of a set of interconnected calculation units which are generally referred to as "nodes." The "nodes" may also be called "neurons." The neural network includes one or more nodes.

The data structure may include data input to the neural network. The data structure including the data input to the neural network may be stored in the computer readable medium. The data input to the neural network may include training data input in the training process of the neural network and/or input data input to the training completed neural network. The data input to the neural network may include data that has undergone pre-processing and/or data to be pre-processed. The pre-processing may include a data processing process for inputting data to the neural network. Accordingly, the data structure may include data to be pre-processed and data generated by the pre-processing. The foregoing data structure is merely an example, and the present disclosure is not limited thereto.

The data structure may include a weight of the neural network. (in the present specification, weights and parameters may be used with the same meaning.) Further, the data structure including the weight of the neural network may be stored in the computer readable medium. The neural network may include a plurality of weights. The weight is variable, and in order for the neural network to perform a desired function, the weight may be varied by a user or an algorithm. For example, when one or more input nodes are connected to one output node by links, respectively, the output node may determine a data value output from the output node based on values input to the input nodes connected to the output node and the weight set in the link corresponding to each of the input nodes. The foregoing data structure is merely an example, and the present disclosure is not limited thereto.

For a non-limited example, the weight may include a weight varied in the neural network training process and/or the weight when the training of the neural network is completed. The weight varied in the neural network training process may include a weight at a time at which a training cycle starts and/or a weight varied during a training cycle. The weight when the training of the neural network is completed may include a weight of the neural network completing the training cycle. Accordingly, the data structure including the weight of the neural network may include the data structure including the weight varied in the neural network training process and/or the weight when the training of the neural network is completed. Accordingly, it is assumed that the weight and/or a combination of the respective weights are included in the data structure including the weight of the neural network. The foregoing data structure is merely an example, and the present disclosure is not limited thereto.

The data structure including the weight of the neural network may be stored in the computer readable storage medium (for example, a memory and a hard disk) after undergoing a serialization process. The serialization may be the process of storing the data structure in the same or different computing devices and converting the data structure into a form that may be reconstructed and used later. The computing device may serialize the data structure and transceive the data through a network. The serialized data structure including the weight of the neural network may be reconstructed in the same or different computing devices through deserialization. The data structure including the weight of the neural network is not limited to the serialization. Further, the data structure including the weight of the neural network may include a data structure (for example, in the non-linear data structure, B-Tree, Trie, m-way search tree, AVL tree, and Red-Black Tree) for improving efficiency of the calculation while minimally using the resources of the computing device. The foregoing matter is merely an example, and the present disclosure is not limited thereto.

The data structure may include a hyper-parameter of the neural network. The data structure including the hyper-parameter of the neural network may be stored in the computer readable medium. The hyper-parameter may be a variable varied by a user. The hyper-parameter may include, for example, a learning rate, a cost function, the number of times of repetition of the training cycle, weight initialization (for example, setting of a range of a weight value to be weight-initialized), and the number of hidden units (for example, the number of hidden layers and the number of nodes of the hidden layer). The foregoing data structure is merely an example, and the present disclosure is not limited thereto.

Figure 9:
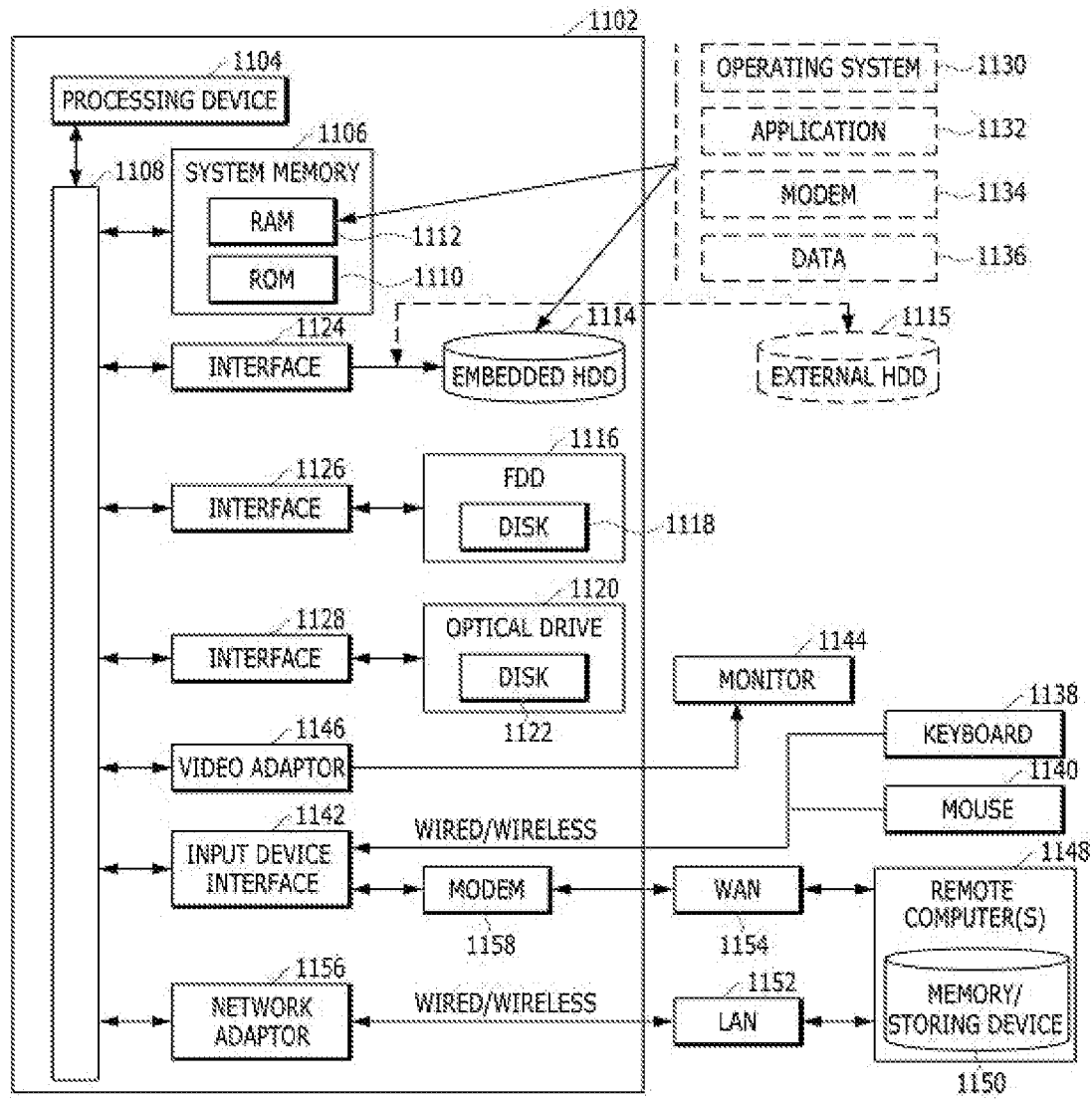
FIG. 9 is a schematic diagram of a computing environment according to an embodiment of the present disclosure.

FIG. 9 is a simple and normal schematic view of a computing environment in which the embodiments of the present disclosure may be implemented.

It is described above that the present disclosure may be generally implemented by the computing device, but those skilled in the art will well know that the present disclosure may be implemented in association with a computer executable command which may be executed on one or more computers and/or in combination with other program modules and/or as a combination of hardware and software.

In general, the program module includes a routine, a program, a component, a data structure, and the like that execute a specific task or implement a specific abstract data type. Further, it will be well appreciated by those skilled in the art that the method of the present disclosure can be implemented by other computer system configurations including a personal computer, a handheld computing device, microprocessor-based or programmable home appliances, and others (the respective devices may operate in connection with one or more associated devices as well as a single-processor or multi-processor computer system, a mini computer, and a main frame computer.

The embodiments described in the present disclosure may also be implemented in a distributed computing environment in which predetermined (or selected) tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media. The computer readable storage media include volatile and non-volatile media, temporary and non-temporary media, and movable and non-movable media implemented by a predetermined (or selected) method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined (or selected) other media which may be accessed by the computer or may be used to store desired information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal obtained by configuring or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An environment 1100 that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined (or selected) processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting.

The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined (or selected) data in an appropriate digital format. In the description of the computer readable media, the mobile optical media such as the HDD, the mobile magnetic disk, and the CD or the DVD are mentioned, but it will be well appreciated by those skilled in the art that other types of media readable by the computer such as a zip drive, a magnetic cassette, a flash memory card, a cartridge, and others may also be used in an operating environment and further, the predetermined (or selected) media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor 1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer(s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is and other means configuring a communication link among computers may be used.

The computer 1102 performs an operation of communicating with predetermined (or selected) wireless devices or entities which are disposed and operated by the wireless communication, for example, the printer, a scanner, a desktop and/or a portable computer, a portable data assistant (PDA), a communication satellite, predetermined (or selected) equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11(a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands).

It will be appreciated by those skilled in the art that information and signals may be expressed by using various different predetermined (or selected) technologies and techniques. For example, data, instructions, commands, information, signals, bits, symbols, and chips which may be referred in the above description may be expressed by voltages, currents, electromagnetic waves, magnetic fields or particles, optical fields or particles, or predetermined (or selected) combinations thereof.

It may be appreciated by those skilled in the art that various logical blocks, modules, processors, means, circuits, and algorithm steps described in association with the embodiments disclosed herein may be implemented by electronic hardware, various types of programs or design codes (for easy description, herein, designated as software), or a combination of all of them. In order to clearly describe the intercompatibility of the hardware and the software, various components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various embodiments presented herein may be implemented as manufactured articles using a method, an apparatus, or a standard programming and/or engineering technique. The term manufactured article includes a computer program, a carrier, or a medium which is accessible by a predetermined (or selected) computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information.

It will be appreciated that a specific order or a hierarchical structure of steps in the presented processes is one example of accesses. It will be appreciated that the specific order or the hierarchical structure of the steps in the processes within the scope of the present disclosure may be rearranged based on design priorities. Appended method claims provide elements of various steps in a sample order, but the method claims are not limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be interpreted within the widest range which is coherent with the principles and new features presented herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for analyzing a lesion based on a medical image, the method performed by a computing device including at least one processor, the method comprising:
   obtaining positional information of the lesion which exists in the medical image based on a probability value for lesion existence of at least one region of interest included in the medical image;
   generating masks for an entire region of the lesion and a region representing a specific attribute of the lesion based on a patch of the medical image corresponding to the positional information; and
   determining a class for a state of the lesion based on the patch of the medical image and the masks,
   wherein the obtaining the positional information of the lesion includes:
   generating the probability value for the lesion existence of the at least one region of interest and candidate positional information included in the medical image by using a pre-trained first model; and
   determining the positional information of the lesion from the candidate positional information based on the probability value for the lesion of the at least one region of interest by using the pre-trained first model.

2. The method of claim 1, wherein the generating the masks for the lesion includes:
   extracting the patch corresponding to the positional information in the medical image; and
   generating a first mask for the entire region of the lesion and a second mask for the region representing the specific attribute of the lesion based on the patch by using a pre-trained second model.

3. The method of claim 2, further comprising:
   generating first numerical information including at least one of a diameter or a volume for the entire region of the lesion based on the first mask; and
   generating second numerical information including at least one of a diameter or a volume for the region representing the specific attribute of the lesion based on the second mask.

4. The method of claim 3, further comprising:
   calculating an evaluation score for the lesion based on the class for the state of the lesion and the first numerical information based on an auxiliary index of diagnosis of a lung disease.

5. The method of claim 4, further comprising:
   generating a user interface based on at least one of the positional information of the lesion, the masks, the class for the state of the lesion, the first numerical information, the second numerical information, or the evaluation score.

6. The method of claim 4, further comprising:
   checking whether a subject of the medical image and a subject of a pre-analyzed image correspond to each other; and
   modifying the evaluation score of the medical image or the evaluation score of the pre-analyzed image based on photographing time points of the medical image and the pre-analyzed image by using a pre-trained fourth model when the subject of the medical image and the subject of the pre-analyzed image correspond to each other.

7. The method of claim 3, further comprising:
calculating an evaluation score for the lesion based on the class for the state of the lesion, the first numerical information, and the second numerical information based on an auxiliary index of diagnosis of a lung disease when the class for the state of the lesion corresponds to a predetermined type for the specific attribute of the lesion.

8. The method of claim 7, further comprising:
generating a user interface based on at least one of the positional information of the lesion, the masks, the class for the state of the lesion, the first numerical information, the second numerical information, or the evaluation score.

9. The method of claim 7, further comprising:
checking whether a subject of the medical image and a subject of a pre-analyzed image correspond to each other; and
modifying the evaluation score of the medical image or the evaluation score of the pre-analyzed image based on photographing time points of the medical image and the pre-analyzed image by using a pre-trained fourth model when the subject of the medical image and the subject of the pre-analyzed image correspond to each other.

10. The method of claim 9, wherein the modifying the evaluation score of the medical image or the evaluation score of the pre-analyzed image includes:
performing registration between the medical image and the pre-analyzed image by using the fourth model;
matching the lesion which exists in the medical image and the lesion which exists in the pre-analyzed image by using the fourth model, and identifying changed information of the matched lesion; and
modifying the evaluation score of the medical image or the evaluation score of the pre-analyzed image based on the changed information.

11. The method of claim 9, wherein the modifying the evaluation score of the medical image or the evaluation score of the pre-analyzed image includes:
modifying the evaluation score of the pre-analyzed image based on the evaluation score of the medical image by using the fourth model when the medical image is photographed at a time point before the pre-analyzed image; and
modifying the evaluation score of the medical image based on the evaluation score of the pre-analyzed image by using the fourth model when the medical image is photographed at a time point after the pre-analyzed image.

12. The method of claim 3, further comprising:
estimating malignancy score of the lesion based on the positional information of the lesion, the class for the state of the lesion, and the first or second numerical information by using a pre-trained fifth model.

13. The method of claim 12, further comprising:
generating a user interface based on at least one of the positional information of the lesion, the masks, the class for the state of the lesion, the first numerical information, the second numerical information, or the malignancy score.

14. The method of claim 3, further comprising:
estimating the malignancy score of the lesion based on the patch and the masks by using a pre-trained fifth model.

15. The method of claim 14, further comprising:
generating a user interface based on at least one of the positional information of the lesion, the masks, the class for the state of the lesion, the first numerical information, the second numerical information, or the malignancy score.

16. The method of claim 1, wherein the determining the class for the state of the lesion includes:
determining at least one of a type for an attribute of the lesion, whether spiculation is made, or whether calcification is made through different sub models based on the patch and the masks by using a third model including at least one pre-trained sub model.

17. A computing device analyzing a lesion based on a medical image, the computing device comprising:
a processor including at least one core;
a memory including program codes executable in the processor; and
a network unit receiving a medical image,
wherein the processor is configured to:
obtain positional information of the lesion which exists in the medical image based on a probability value for lesion existence of at least one region of interest included in the medical image,
generate masks for an entire region of the lesion and a region representing a specific attribute of the lesion based on a patch of the medical image corresponding to the positional information, and
determine a class for a state of the lesion based on the patch of the medical image and the masks,
wherein the processor is further configured to:
generate the probability value for the lesion existence of the at least one region of interest and candidate positional information included in the medical image by using a pre-trained first model; and
determine the positional information of the lesion from the candidate positional information based on the probability value for the lesion of the at least one region of interest by using the pre-trained first model.

18. A user terminal comprising:
a processor including at least one core;
a memory;
a network unit receiving a user interface based on analysis information of a lesion included in a medical image from a computing device; and
an output unit providing the user interface,
wherein the analysis information of the lesion includes at least one of positional information of the lesion, masks for an entire region of the lesion and a region representing a specific attribute of the lesion, a class for a state of the lesion, numerical information of the lesion, evaluation information for the lesion, or malignancy score of the lesion,
wherein the positional information of the lesion which exists in the medical image is obtained based on:
generating a probability value for lesion existence of at least one region of interest and candidate positional information included in the medical image by using a pre-trained first model; and
determining the positional information of the lesion from the candidate positional information based on the probability value for the lesion of the at least one region of interest by using the pre-trained first model.

* * * * *